United States Patent [19]

Redenbaugh et al.

[11] Patent Number: 4,777,762
[45] Date of Patent: * Oct. 18, 1988

[54] DESICCATED ANALOGS OF BOTANIC SEED

[75] Inventors: M. Keith Redenbaugh; David Slade; Jo A. Fujii, all of Davis, Calif.

[73] Assignee: Plant Genetics, Inc., Davis, Calif.

[*] Notice: The portion of the term of this patent subsequent to Apr. 22, 2003 has been disclaimed.

[21] Appl. No.: 946,062

[22] Filed: Dec. 24, 1986

Related U.S. Application Data

[63] Continuation-in-part of Ser. No. 816,889, Jan. 7, 1986, which is a continuation-in-part of Ser. No. 433,688, Oct. 12, 1982.

[51] Int. Cl.$^4$ ............................................... A01C 1/06
[52] U.S. Cl. ................................... 47/57.6; 47/DIG. 9
[58] Field of Search ................... 47/58, 57.6, DIG. 9

[56] References Cited

U.S. PATENT DOCUMENTS

| | | | |
|---|---|---|---|
| 2,967,376 | 1/1961 | Scott | 47/58 X |
| 4,241,537 | 12/1980 | Wood | 47/57.6 X |
| 4,245,432 | 1/1981 | Dannelly | 47/57.6 |
| 4,562,663 | 1/1986 | Redenbaugh | 47/58 |
| 4,615,141 | 10/1986 | Janick et al. | 47/57.6 |

Primary Examiner—Robert E. Bagwill
Attorney, Agent, or Firm—Limbach, Limbach & Sutton

[57] ABSTRACT

Methods and materials are provided for desiccated analogs of botanic seeds which are created by removing a portion of the water by slow or fast drying so that the plant tissue is no longer saturated with water. In a second embodiment, the meristematic tissue is encapsulated in a gel or polymer followed by dehydration. In another embodiment, the meristematic tissue is dehydrated prior to encapsulation in a gel. Protectants can be incorporated in the gel capsule. Meristematic tissue can be isolated from, for example, somatic embryos, zygotic and germ line sources.

33 Claims, No Drawings

DESICCATED ANALOGS OF BOTANIC SEED

DESCRIPTION

RELATED APPLICATIONS

This application is a Continuation-in-Part of commonly owned and copending application Ser. No. 06/816,889, filed Jan. 7, 1986, which is a Continuation-in-Part of commonly owned and copending application Ser. No. 433,688, filed Oct. 12, 1982.

TECHNICAL FIELD

This invention relates generally to the field of agriculture and crop production and more particularly to the production of plant reproductive units which are analogs of botanic seed wherein the genotype may be identical to the parental strain.

BACKGROUND OF THE INVENTION

The conventional techniques of crop improvement in agriculture involve a search for strains of plants which exhibit new and useful characteristics, or to refine and improve on existing ones. The search has evolved from mere selection of a desirable parent plant to hybridization between parental strains which each exhibit desirable characteristics, finally, to crossbreeding between homozygous strains such that identical $F_1$ progeny will be produced in each subsequent crossbreeding.

The conventional methods of maintaining genetic identity are well known and described in the literature. See, e.g., R. W. Allard "Principles of Plant Breeding," (John Wiley and Sons, Inc., 1960). The maintenance of purebred strains and the repeated crossbreeding to obtain $F_1$ progeny are time consuming and labor intensive.

An additional limitation on the sexual reproduction of parental strains has been the low seed productivity per plant. This often results from low vigor which is manifested by heavily inbred strains. Finally, only a relatively limited number of purebred lines may be produced, and this results in a decreased pool of genetic characteristics available for selection.

It has been recognized that some of these difficulties may be overcome by vegetative propagation of the parental strain. See: W. C. Anderson and J. B. Carstens, "Tissue Culture Propagation of Broccoli, *Brassica oleracea* (Italica Group), for use in $F_1$ Hybrid Seed Production," J. Amer. Soc. Hort. Sci., 102(1), pp. 69–73 (1977). This technique avoids the problem of the change in parental strain genetic characteristics through sexual reproduction. However, the sexual cross to produce $F_1$ seed does not guarantee uniform progeny where there is chromosomal trait segregation in the parental strains.

It has been suggested that a desirable species may be propagated vegetatively with the somatic embryos or rooted plantlets being transferred to the field. However, this technique involves skilled labor in tissue culture laboratories, a transfer to a hothouse or nursery, and upon attaining sufficient acclimatization, a transplantation to the field. This procedure is costly and time consuming in comparison with the traditional methods of seeding.

To overcome some of these difficulties, the technique of fluid drilling has been developed. Fluid drilling methods have been used with pregerminated seed, e.g., D. Gray, "Comparison of Fluid Drilling and Conventional Establishment Techniques on Seedling Emergence and Crop Uniformity in Lettuce," J. Hort. Science, 52:23–30 (1978), and it has been suggested that fluid drilling may be adaptable to transfer somatic embryos directly to the field, e.g., D. A. Evans and W. R. Sharp, "Application of Tissue Culture Technology in the Agricultural Industry," in Application of Plant Cell and Tissue Culture to Agriculture and Industry, D. T. Tomes et al., eds. (University of Guelph Press, pp. 212–13, 1982). HoweVer, fluid drilling technology is capital intensive and requires the purchase of machinery and the development of new techniques in the agricultural community, which has been historically resistant to such change. Furthermore, fluid drilling does not allow for precision planting of seeds or somatic embryos.

To overcome the difficulties of fluid drilling, the creation of artificial seeds has been proposed in which somatic embryos are singly encapsulated in a hydrated gel consisting of 3.2% gel and 96.8% water (e.g., K. Redenbaugh, J. Nichol, M. E. Kossler, and B. Paasch, "Encapsulation of Somatic Embryos for Artificial Seed Production," In Vitro 20:256–257, 1984). The resultant hydrated capsule containing plant tissue can then be planted using traditional vacuum pick-up seed planters. However, the hydrated gel capsule contains encapsulated plant tissue that is also hydrated, consisting of a level of water equal to that of the gel capsule. When encapsulated, previously desiccated meristematic tissue, somatic embryos, or tissue-cultured plants would imbibe water to the level of the hydrated gel.

It has been suggested that somatic embryos be dried in a solution of polyethylene oxide. See: S. L. Kitto and Jules Janeck, "Production of Synthetic Seeds by Encapsulating Asexual Embryos of Carrot," J. Amer. Soc. Hort. Sci. 110(2):277–282 (1985). However, uncoated embryos did not survive desiccation. Furthermore, although coated clumps of embryos survived, no complete plants were produced.

This invention recognizes that the desiccation of plant tissue to a water content less than that of saturation of plant tissue may allow for more complete development and maturation, so that more vigorous, clonally uniform, and complete plants are formed. Furthermore, desiccated plant tissue may be more analogous to true seeds in terms of hydration level. Consequently, the desiccated plant tissue may be handled, stored, and treated in a manner closely analogous to true seeds.

Thus, an object of the invention is to provide a technique whereby cultured plant tissue may be insulated from harmful conditions.

Another object is to induce further maturation of the meristematic tissue, somatic embryos, or tissue-cultured plants, so that the plant tissue more readily, quickly, and uniformly forms a complete plant.

Still another object is to produce hardier and more developmentally complete meristematic tissue, somatic embryos, or tissue-cultured plants.

Another object is to control the developmental progression of plant tissue so that somaclonal and other variation are reduced or eliminated.

Yet another object is to reduce the water content of the plant tissue so that metabolism, DNA synthesis, and cell division are reduced and developmental arrest insues, allowing for an improved plant tissue with increased shelf life.

A further object is to desiccate the plant tissue so that DNA repair occurs.

Yet a further object is to desiccate the plant tissue to turn off development genes and turn on germination and growth genes.

Still another object is to desiccate the plant tissue so that hormone balance and plasma membrane integrity are achieved allowing for more complete maturation and whole plant recovery.

An additional object is to provide a clonal propagation system for genetically improved or transformed plants in which the modified genes or chromosomes are not stably integrated into the plant genome.

Another object of this invention is to decrease the time for raising a mature or vigorous seedling from meristematic tissues, somatic embryos or tissue-cultured plants.

Yet another object of the invention is to provide a medium to deliver the cultured plant tissue together with adjuvants facilitating seedling stand establishment.

A further object of the invention is to reduce the amount of handling between the development of the cultured plant tissue and its planting in the field.

A still further object of the invention is to reduce the need for special handling techniques and special technology during the development and growth of cultured plant tissue and, thus, overcome resistance to the introduction of new technology by adapting to existing methods of seed planting technology.

An additional object of the invention is to provide a large scale, economical method to clone superior plants or hybrid plants.

DISCLOSURE OF INVENTION

Briefly, in accordance with the invention, desiccated analogs of botanic seed are created by encapsulating totipotent meristematic tissue in a gel or polymer and removing a portion of the water by slow or fast drying so that the plant tissue is no longer saturated with water.

In accordance with another aspect of the invention, totipotent meristematic tissue is dehydrated by a slow or fast process so that the plant tissue is no longer saturated with water. Such dehydrated meristematic tissue is planted directly with or without a subsequent coating.

In accordance with one aspect of the invention, meristematic tissue is isolated by inducing the formation of somatic embryos. These embryos are then encapsulated in a gel or polymer and dehydrated to remove a portion of the water, so that the plant tissue is no longer saturated with water. During the drying process, the embryo may continue development.

In accordance with another aspect of the invention, meristematic tissue is isolated from somatic sources and, having the potential to differentiate to produce an entire plant body, is encapsulated without somatic embryogenesis being induced.

In accordance with another aspect of the invention, meristematic tissue is isolated from zygotic or germ line sources, removed from the seed coat, and encapsulated in a gel or polymer which is dehydrated to remove a portion of the water.

In accordance with yet another aspect of the invention, meristematic tissue is isolated by inducing the formation of somatic embryos. These embryos are then desiccated to less than complete tissue saturation during, or at the end of, embryo development.

The invention is particularly advantageous in creating desiccated analogs to botanic seed which promote the delivery of superior clones or hybrids to the field using traditional planting methods.

BEST MODE FOR CARRYING OUT THE INVENTION

Plant meristematic tissues are units of organization. Some meristematic tissues have the capacity to produce an entire plant body; others produce only selected tissues. Those which produce an entire plant body are termed totipotent. It is an inherent property of an embryo to recapitulate ontogeny. This capacity resides in the meristem, and the other structures in a seed or embryo are accessory to this meristematic tissue.

Zygotic embryos with the seed coat removed can be encapsulated in accordance with the present invention to provide the necessary meristematic tissue. Meristematic tissue, termed totipotent, can also be isolated from many sources, including the induced formation of such tissue from the somatic tissue of a plant.

The accessory structures and compounds normally included with meristematic tissue can be substituted or supplemented by various adjuvants including microorganisms and biologically active compounds which will modify the plant or its environment to enable the tissue to thrive and compete more successfully for resources. These various adjuvants can be mixed together in a homogenous solution and subsequently gelled. Alternatively, the components can be injected into a preformed gel or layered onto a core (containing for example meristematic tissue) to build up a multilayered capsule with components arranged in a specific order for delivery and release. As an additional alternative, the various components of the capsule can be microencapsulated or otherwise treated to impede or control other adjuvants or materials from within the capsule. As a further alternative, the components can be incorporated into the gel as the gel is desiccating.

In accordance with one aspect of the invention, meristematic tissue and adjuvants are combined for delivery by encapsulating the components in a gel or polymer and subsequently drying to remove a portion of the water. The gel or polymer can control germination and development of the meristematic tissue as well as the release and function of the adjuvants. Further, in accordance with another aspect of the invention, meristematic tissue and adjuvants are combined for delivery during tissue desiccation.

Selection of Meristematic Tissue

Botanic seed is one mechanism which has evolved to allow delivery of the progeny of plants to sites which are suitable for development and growth. The essential element of botanic seed is the meristematic tissue which differentiates to form an entire plant body.

Botanic seed is readily available from most plant and crop species. Seed production methods are well known to the industry. See, e.g., J. Janick, R. W. Schery, F. W. Woods, V. W. Ruttan, "Plant Science" (W. H. Freeman, San Francisco, 1974); and H. T. Hartmann and D. E. Kester, "Plant Propagation" (Prentice-Hall, Englewood Cliffs, N.J., 1975). It is therefore intended that any available botanic seed with the seed coat removed can be encapsulated in accordance with the present invention.

Cultured plant tissue can be isolated from numerous sources, including somatic tissue, zygotic tissue, or germ line tissue. Regardless of its source, the tissue must pass through a meristem stage in order to undergo organogenesis and develop into a regenerated plant body.

Somatic tissue sources which are not ordinarily involved in reproduction can, under appropriate circumstances of inducement, form meristematic tissue.

As a first step in the production of encapsulated somatic embryos, crop strains must be selected which are capable of somatic embryogenesis. For a representative list of such species, see D. A. Evans and D. R. Sharp, "Application of Tissue Culture Technology in the Agricultural Industry," in Application and Plant Cell and Tissue Culture to Agriculture and Industry, D. T. Tomes et al., editors, (University of Guelph Press, page 214, 1982). Further species may be shown capable of somatic embryogenesis with further experimentation and refinement of technique.

Once the appropriate strain is selected, preparation of somatic embryos can proceed by any of the numerous known techniques. For example, in alfalfa, see K. A. Walker and S. J. Sato, "Morphogenesis in Callus Tissue of Medicago sativa: the Role of Ammonium Ion in Somatic Embryogenesis," Plant Cell Tiss. Org. Cult. 1:109–121 (1981). For other techniques known to the art, see e.g., Street, H. E., ed., "Plant Tissue and Cell Culture," University of Califonia Press (1977).

The somatic tissue of certain other species are able to undergo shoot organogenesis without the intermediate formation of somatic embryos. See, T. Murashige, "Plant Propagation Through Tissue Culture," Ann. Rev. Plant Physiol. 25:135–146 (1974). Tissue from these plants may be encapsulated without the preliminary embryogenesis step, and mature plants grown therefrom.

As an alternative, zygotic embryos can be used when, for example, the species is incapable of somatic embryogenesis. These zygotic embryos can be grown in culture or suspension, and then be encapsulated without their natural seed coat.

In certain wide crosses, a fertile embryo is formed but the endosperm fails to develop and the embryo then dies. Thus, the cross appears sterile, but viable progeny can be obtained by isolating the embryo from the aborted ovule. The zygotic embryos may be separated from their seed coat and then encapsulated with adjuvants which will enhance their growth and viability. See, for example, M. Monnier, "Culture of Zygotic Embryos," Frontiers of Plant Tissue Culture, T. A. Thorpe, ed. (The International Association for Plant Tissue Culture, University of Calgary, Alberta, Canada, pp. 277–280, 1978).

Encapsulation Media Gels

It has been recognized that the germination and development of seeds may be enhanced by coating them with various materials. For example, it has been reported that coating seeds with Super Slurper (USDA) will result in a water-absorbent reservoir which improves germination rate in arid conditions.

It has been demonstrated that perishable foods may be preserved by coating them with a complexed carbohydrate, e.g., Earle U.S. Pat. No. 3,395,024. There are also reports of seeds coated with dried materials, using e.g., alginate as a binding compound, U.S. Pat. Nos. 3,545,129 and 3,698,133; Dexter, S. T. and T. Miyamota, Agron J., 51:338 (1959).

Meristematic tissue can be encapsulated in accordance with the present invention in any of the numerous media or polymers which provide an appropriate encapsulation matrix, hereafter termed "gel". In general, a gel will allow meristem or embryo respiration by permitting diffusion of gases. The gel should provide a capsule strong enough to resist external abrasion and adverse forces, yet pliable enough to allow the growth of the embryo and its germination at the appropriate time.

Gels finding use in the present invention are preferably, but not exclusively, hydrogels or polymers which contain water within the confines of the gel matrix but which can be dried as the plant tissue is being desiccated or which can be placed around a dried embryo in a dry form. It may be desirable to use various gels in combination, either as a mixture or in layers, to achieve the desired results. The gel itself may serve as a protectant to the plant tissue as it is being dried.

Gels which have been found useful for encapsulating meristematic tissue in a desiccated form include sodium alginate, Tullanox TM (fumed silica, Tulco ®, Inc., Ayer, Mass., 01432), and Terra-sorb TM (a gelatinized, starch-hydrolyzed polyacrylonitrile graft copolymer, Industrial Services International, Inc.). Other suitable polymers include, but are not limited to:

TABLE 1. GEL AGENTS

I. Natural Polymers

A. Ionic bonds (requires complexing agents)
  Alginate with Gelatin
  Sodium Pectate
  Furcellaran
  Pectin
  Hypnean
  Dextran
  Tamarind
  Guar Gum
B. Hydrophobic Interactions
  Amylose
  Agar
  Agarose
  Agar with Gelatin
  Gelatin
  Starch
  Amylopectin
  Cornhull Gum
  Starch Arabogalactan
  Gum Ghatti
  Gum Karagan
  Ti Gum
  Gum Tragacanth
  Wheat Gum
  Chitin
  Dextrin II. Chemically Modified Natural Polymers A. Ionic Bonds (requires a complexing agent)
  Ethyl Succinylated Cellulose
  Succinylated Zein
  Carboxymethylcellulose
B. Hydrophobic Interactions
  Methylcellulose
  Hydroxyethyl Cellulose
C. Covalent Bonds
  Gelatin with Glutaraldehyde III. Synthetic Polymers A. Covalent Bonds
  Polyacrylamide
B. Hydrophobic Interactions
  Polyethylene Glycol Polyvinylpyrrolidone
Polyoxyethylene
Hydrophilic Urethane
Polyvinylacetate
Vinyl Resins
Hydron (hydroxyethylmethacrylate)
2-methyl-5-vinylpyridine-methylacrylate-methacrylic acid C. Ionic Bonds
  Sodium poly (styrene sulfonate) with poly (vinyl methyl pyridinium) chloride
  Sodium poly (styrene sulfonate) with poly (vinyl benzyl trimethyl ammonium) chloride
  Strongly acidic polyanion with strongly basic polycation
  Bordon Poly Co. 2113 ® (vinyl acetate homopolymer) (Borden Co.)
  Gelvatol ® (polyvinyl alcohol resin) (Monsanto)

IV. Stabilizing Compounds
A. Trade Names
  Super Sluper ® (USDA, SEA-AR, Nor. Reg. Res. Lab)
  Viterra ® (Union Carbide)
  Laponite ® (Laporte (United States) Inc.)
  Gelrite ® (Kelco)
  SeaKem ® (FMC Corporation)
  SeaPlaque ® (FMC Corporation)
  SeaPrep ® (FMC Corporation)
  IsoGel ®(FMC Corporation)
B. Organic Compounds
  Methylan Clear Wallpaper Paste
  Lactose
  Wax
  Protein colloids
C. Inorganic Compounds
  1. Clay
  2. Compounds that adhere by means of water water-soluble plastic such as methylcel:
     Fly Ash
     Feldspar
     Celrite
     Bentonite
     Vermiculite
     Diatomaceous Earth
     Lime
     Calcium Carbonate
  3. Other
     Calcium Oxide
     Magnesium Carbonate
     Sodium Bicarbonate
     Urea Selecting Optimum Gels A gel chosen for encapsulation would usually include the following characteristics (although the invention may be practiced in other modes):

1. A compliance adequate to protect and cushion the meristem;
2. The interior material would have solubility or emulsion forming characteristics such that it can accept and contain adjuvants, including but not limited to aqueous or hydrophobic substances;
3. An outer surface to provide a protective barrier to mechanical stress, facilitate handling and maintain meristem viability;
4. Sufficient gel strength to maintain capsule integrity but still allow the meristem to break out during germination and to release the adjuvants.
5. An ability to be dried to less than the saturation point without harming the enclosed meristem.

Selection of Adjuvants

It has been recognized that plant establishment, growth and development may be enhanced by the addition of adjuvants to the soil, to the rhizophere of the plant, and to the surface of the plant. It has also been demonstrated that controlled release of the adjuvants may provide additional enhancement to plant growth. See, T. J. Roseman and S. Z. Mansdorf "Controlled Release Delivery Systems," (Marcel Dekker, Inc., N.Y., 1983). Furthermore, it has been recognized that plant tissue undergoing freezing for cryopreservation requires a protectant. See, K. K. Kartha, "Cryopreservation of Plant Cells and Organs," (Newsletter International Association for Plant Tissue Culture, No. 45, pp. 2-15, 1985).

Adjuvants which have been found to be useful for encapsulation and coating with meristematic tissue desiccated to less than saturation include dimethylsulfoxide and dextran.

Other suitable adjuvants include, but are not limited to:

TABLE 2. ADJUVANTS

I. Protectants
  A. Permeating Compounds
    1. Sucrose
    2. Glucose
    3. Calcium chloride
    4. Potassium chloride
    5. Trehalose
    6. Glycerol
    7. Proline
  B. Non-permeating Compounds
    1. Polyvinylpyrrolidone
    2. Hydroxyethyl starch
    3. Mannitol
    4. Sorbitol
    5. Polyethylene glycol
    6. Oligosaccharides
    7. Polyamines
    8. Alpha-tocopherol (Vitamin E)

II. Pesticides

A. Herbicides
  1. Phenoxy compounds
     2,4-D
     MCPB
     2,4,5-T
     Bifenox
  2. Benzoic, acetic acids, and phthallic compounds
     Chloramben
     Dicamba
     Bromoxynil
     Chlorthiamid
  3. Dinitro anilines, nitrites, amides, acetamides and anilides
     Triflualin
     Benefin
     Oryzalin
  4. Carbamates
     Butylate
     Asulam
     Thiobencard
  5. Heterocyclic nitrogen derivatives
     Picloram Aminotriazole
Paraquate
Simazine
6. Urea compounds
   Diuron
   Bromacil
   Terbacil
   Isoproturon
7. Metal organics and inorganics
   DSMA
8. Other herbicides
   Petroleum oils
   Aromatic oils
   Oxyfluorfen
   Bentazon
   Fluridome
   Bensulide
   EPTC
   Metribuzin
   Pebulate
   Prometryn
   Pronamide
   Chlorpropham
   Alachlor B. Insecticides 1. Cyclo compounds
   Endrin
   Heptachlor
   Lindane
   Mirex
   Diazinon
2. Carbamate
   Carbofuran
   Isoprocarb
3. Animal plant derivation and inorganic compounds
   Rotenone
   Thiocyclam
4. Diphenyl compounds
   DDT
   Methoxychlor
   Difluron
   Amitraz
5. Organic phosohates
   Dicrotophos
   Parathion
   Malathion
   Phorate
   Phosmet
   Penncap M ® (Pennwalt Corp.)
   KnoxOut 2FM ® (Pennwalt Corp.)

C. Fungicides
1. Inorganics
   Copper sulfate
2. Metal organics
   Cadminate (Mallinckrodt Chemical Works)
3. Antibiotics and bacteriocins
   Streptomycin
   Cycloheximide
   Piomy
4. Carbamates
   Ferbam
   Ziram
   Thiram
5. Organic fungicides
   Carboxin
   Captan
   Chloroneb
   Benomyl
   Metalaxyl D. Fumigants, Repellents, and Rodenticides
1. Fumigants
   Methyl bromide
   Carbon bisulfide
   Propylene dichloride
   Vapam
2. Repellents
   Thiram
   Protect
3. Rodenticides
   Warfarin
   Endrin II. Fertilizers and Nutrients Superphosphate
Calcium phosphate
Potassium phosphate
Potassium nitrate
Calcium nitrate
Ammonium nitrate
Nitrogen
Phosphate
Potassium
Sulfur
Calcium
Magnesium
Amino acids IV. Energy Sources Sugars
Carbohydrates
ATP V. Microorganisms

*Eschericia coli*
Azospirillum species
Pseudomonas species
Azotobacter species
Cyanobacteria
*Bacillum thuringiensis*
Mycorrhizal fungi
Rhizobia species
*Bacillus subtilis*
*Bacterioides ruminicola*
*Lachnospira multiparus*
*Aspergillus fumigates*
*Fusarium oxysporum*
Paecilomvces species
Flavobacterium species
Achromobacter species
Aspergillus species
Arthobacter species
Actinomycete species
Halophytic bacteria
Nitrosomonas species
Nitrobacter species
Sulfur mineralizng bacteria
Baculovirum species
*Heliothis zea* NPV
*Autographa Californica* NPV VI. Growth Regulators and Hormones Giberellic acid
Cytokinins
Ethoxyquin Naphthalene acetic acid
Indolebutyric acid
Para-chlorphenoxyacetic acid Ethylene
Indole acetic acid

VII. Other Biologically Active Components

Denitrification inhibitors
Iron chelators
Pheromones
Enzymes
Pesticide Antidotes and Safeners

VIII. Other Inert Components

Soil and water conditioners Dispersants
Wetting agents
pH altering compounds
Water absorbing compounds

Encapsulation with Selected Gel

Once the gel has been chosen, there are numerous parameters which influence the characteristics previously mentioned.

A sodium alginate solution, for example, will form a gel when a complexing agent is added. Calcium chloride ($CaCl_2$) is generally used, however, lanthamum chloride, ferric chloride, cobaltous chloride, calcium nitrate, calcium hydroxide, superphosphate fertilizer, and many pesticides such as benefin, alachlor and chlorpropham are also acceptable, as are other compounds generally with multivalent cations.

A selected gel will have a range of concentrations usable in working the invention. A concentration should be chosen to optimize ease of handling, gelling time, strength of gel and coating thickness around the meristematic tissue. If the gel is too dilute, the tissue may settle during gel formation and produce an uneven encapsulation. The sodium alginate for example, can be prepared in a concentration of 0.01 to 10% w(in grams)/v (in milliliters) in water and preferably from 0.5 to 5%.

The meristematic tissue to be encapsulated can then be added to the sodium alginate solution at a concentration of 1 to 50 meristems per milliliter, more usually from 5 to 20 meristems per milliliter. This concentration will vary as the appropriate size of meristematic tissue varies with species, source and stage of development.

Specific adjuvants to be encapsulated can then be added to the sodium alginate and meristem solution at concentrations specific for the application rates of the particular adjuvants. Pesticides, for example, can be added at a concentration of 0.0002 to 2.0000 milliliters formulated pesticide ($2 \times 10^{-6}$ to 2 grams active ingredient) per milliliter sodium alginate solution, more usually from 0.002 to 0.200 milliliters formulated pesticide ($2 \times 10^{-4}$ to 0 18 grams active ingredient) per milliliter. Fertilizers, for example, can be added at a concentration of 0.1 to 200 milligrams per milliliter sodium alginate. Microorganisms, for example, can be added at a concentration of 1 to $10^{12}$ microorganisms per milliliter sodium alginate, more usually $10^4$ to $10^{10}$ microorganisms per milliliter. Carbon sources can be added at a concentration of 1 to 500 milligrams per milliliter of sodium alginate solution, more usually 5 to 100 milligrams per milliliter. Protectants can be added at a concentration of 1 to 1,000 milligrams per milliliter of sodium alginate solution, more usually 10 to 500 milligrams per milliliter.

The dispersed adjuvants and meristematic tissue in gel solution can then be added dropwise to the complexing agent. Alternatively, the gel solution and complexing agent may be mixed by any of the numerous techniques known to the art. These may include droplet formation and agent addition as a one step process by a vibrating nozzle which ejects a gel droplet from one source and coats the droplet with a complexing agent from another. As a further alternative, the gel solution with plant tissue can be desiccated to less than total saturation at a saturation level of 0.1 to 99.9 percent, more usually 1 to 80 percent without addition of the complexing agent.

The calcium chloride (or other complexing agent) can be made up in solution at a concentration of 1 to 1,000 millimolar, more usually 20 to 500 millimolar and ideally from 50 to 300 millimolar. Other complexing agents will have different preferred concentration ranges.

The time for gel formation and the temperature of the gelling solutions are interrelated parameters, for selected concentrations of gel and complexing agent. The temperature should be chosen so as to avoid damage to the meristematic tissue, usually in the range of 1° to 50° C., more usually 10° to 40° C., and preferably 20° to 40° C.

Within the range of acceptable temperatures, a particular value can be chosen to give the shortest possible gelling time consistent with complete gel formation. Typically, the gel will form immediately, but the complexation takes much longer. For a solution of sodium alginate at a concentration of 3.2 grams per 100 milliliters $H_2O$, calcium chloride solution concentration of 50 millimolar and 25° C. reaction temperature, adequate gelling is obtained in 5 to 120 minutes, more often 10 to 90 minutes, and is usually sufficiently complete in 20 to 60 minutes. Alternatively, if 300 millimolar calcium chloride is substituted for 50 millimolar calcium chloride, gel time is decreased to 2-5 minutes.

As a further alternative, the complexed gel and plant tissue can be subsequently desiccated to a saturation level of 0.1 to 99.9 percent, more usually 1 to 80 percent.

The desiccation period can be rapid, occurring from one minute to five days, more usually 30 minutes to one day. Alternatively, the desiccation period can be slow, occurring from five days to three months, more usually 7 to 28 days.

The gel characteristics described above are modifiable for each gel, but are determined generally by the concentration parameters and chemical properties of the gel.

Hardening Capsules

Subsequent to encapsulation, it may be desirable to increase the rigidity of the outer surface of the gel matrix, through numerous techniques known to the art. In this manner, a softer gel may be used for the encapsulation and inclusion of appropriate additives and, in the outer surface, resistance to abrasion and penetration may be increased with no loss of meristem viability.

The encapsulated meristematic tissue may be subjected to a partial desiccation, which results in a more rigid outer surface.

Alternatively, the encapsulated meristematic tissue formed of a selected gel may again be coated with a thin layer of a more rigid gel, or may be encased in a gelatin capsule available through commercial sources.

The surface may also be hardened by treatment with various chemical agents known to the art, which increase the gel surface breaking resistance.

Such techniques include, in part:

TABLE 3. CAPSULE COATING COMPOUNDS

I. Coacervation

Gelatin and Gum Arabic
Lecithin and cephalin with cellulose nitrate
Paraffin oil with cellulose nitrate

II. Interfacial Polymerization

Sebacoyl chloride with hexanediamine

III. Tannic Acids

Persimmon tannin
Chinese gallotannin

IV. Poly Amino Acids

Polyornithine
Polylysine
Polycitrulline
Polyarginine
Polyhistidine
Polyglutamine
Combination of Poly-L-Amino acids

V. Glutaraldehyde

Glutaraldehyde with gelatin

VI. Gelatin Capsules

VII. Enteric Coating

Methylvinyl ether/maleic anhydride
Styrene maleic acid copolymer
Styrene-maleic anhydride copolymer
Ethylene/maleic anhydride copolymer

VIII. Hydrophobic Polymers

Ethylcellulose
Isopropyl myristate
Polyvinyl acetate phthalate
Starch acetate phthalate
Cellulose acetate phthalate
Saran
Butyl rubber

IX. Other Compounds

Keratin
Shellac
Carnuba wax
Paraffin
Wax
Fats
Lipids
Triglycerides
Ethylene vinyl acetate copolymer
Benzyl cellulose
Petrolatum
Elvax 4260 ® (ethylene vinyl acetate acrylic acid terpolymer, DuPont, Wilmington, Del.)
Spermaceti Wax Substitute (J. B. Ross Co., Jersey City, N.J.)
Elvax 310 ® (ethylene vinyl acetate copolymer, DuPont)
Gantrez ES-435 ® (GAF Corporation)

In utilizing the means of hardening the outer surface of the gel capsule, care must be taken to avoid damage to the meristematic tissue. For example, crosslinking the gel matrix with glutaraldehyde will provide surface strength, but if the glutaraldehyde is applied for an extended period of time, it will penetrate the gel completely and damage the meristematic tissue. This time period will vary with the gel material, the thickness of the gel coat and the temperature of the solutions.

It has been noted that certain of the abovementioned treatments, e.g., polylysine, will change the water retention characteristics of the gel, but not the breaking strength. Thus, by appropriate combination of treatments, most gel characteristics may be adjusted to their desired values.

Further Modifications

In agricultural applications, it is generally preferred that harvesting be accomplished in a brief period of time and in the appropriate season. Therefore, either before or during the gelling process, it may be desirable to synchronize the germination of the meristems or embryos through techniques known to the art, such as the use of mitotic blockers or sizing through sieves, so that any given batch of encapsulated meristems, somatic embryos, or seeds without the seed coat will germinate at approximately the same time. Various salts may be used to control and impede meristem germination, particularly osmotically active monovalent salts.

High osmotic potentials will also control meristem germination. For example, sucrose at concentrations of 6 to 20% weight in grams per water in liters, more usually 8 to 15%, and ideally 10 to 14% will control germination of Brassica zygotic embryos isolated from the seed coats when encapsulated inside calcium alginate capsules. This germination control was effective for at least one month when the encapsulated Brassica embryos and sucrose were stored in a sealed container. Upon placement on Schenk and Hildebrandt medium (SH) (Can. J. Bot. 50:199-204, 1972) the embryos readily and uniformly germinated at rates equal to controls.

As an alternative to salts or sucrose, abscisic acid affects zygotic embryo germination. For example, abscisic acid at concentrations of $10^{-3}$ to $10^{-6}$ molar, more usually $10^{-4}$ to $10^{-5}$ molar, will similarly control isolated Brassica embryo germination.

As another alternative, storage of encapsulated seeds or embryos at low temperatures, 0° to 10° C., more usually 2° or 8° C. in conjunction with any salts, sucrose, or abscisic acid will also control isolated embryo germination.

Subsequent to encapsulation or planting, it may be desirable to store the encapsulated meristematic tissues, transport them to the field, hothouse or the nursery, and treat them in a manner consistent with botanic seed. These encapsulated meristematic tissues can be planted either in the nursery or in the hothouse for species unable to tolerate the ambient climatic conditions without some period of acclimization. Alternatively, for more hardy species, the encapsulated meristems may be planted directly in the field through numerous techniques employed in the art for botanic seed.

Experimental

In order to demonstrate the invention, the following experiments were carried out with a variety of meristematic tissue material, gel media and adjuvants. All quantities labeled percent (%) are grams per 100 milliliters, unless otherwise indicated.

EXAMPLE A: (ALFALFA SOMATIC EMBRYOS)

1. Naked Alfalfa Somatic Embryos Desiccated Without Medium

Callus from alfalfa, *Medicago sativa* L. strain RA-3, was induced to form somatic embryos by a three to four days exposure to Shenk and Hildebrandt medium (Medium and Techniques for Induction and Growth of Monocotyledenous and Dicotyledenous Cell Cultures Can. J. Bot. 50:199–204, 1972), supplemented with 50 micromolar 2-4-dichlorophenoxyacetic acid (2,4-D) and 5 micromolar kinetin. The tissue was then transferred to a 2,4-D and kinetin-free SH regeneration medium. This procedure is explained in detail in: K. A. Walker, et al. "The Hormonal Control of Organ Formation in Callus of *Medicago sativa* L. Cultured In Vitro," Am. J. Bot. 65:654–659 (1978), K. A. Walker, et al., "Organogenesis in Callus Tissue of *Medicago sativa*, The Temporal Separation of Induction Process from Differentiation Processes," Plant Sci. Lett. 16:23–30 (1979); and D. Stuart and S. Strickland, "Somatic Embryogenesis from Cell Cultures of *Medicago sativa* L.," Plant Sci. Lett. 34:134–181, 1984, as cited elsewhere herein. These articles are incorporated herein by reference.

The alfalfa somatic embryos were air dried without medium at 25° C. under a sterile atmospheric condition of 10–20% relative humidity for 15 to 25 minutes. The somatic embryos were placed on half-strength Shenk and Hildebrandt medium supplemented with 1.5% w/v maltose and 25 µM gibberellic acid rather than 1.5% sucrose to assess survival.

The somatic embryos were dried to 8% of the fresh weight of the fully saturated somatic embryo after 20 minutes. Somatic embryo survival was 43% of the total somatic embryos. The dried somatic embryos germinated at 43% whereas non-dried controls germinated at 30%.

1a. As an alternative drying duration, the somatic embryos were dried 15 minutes and survival was 88%.

1b. As an alternative dry weight, the somatic embryos were dried to 64% of their fresh weight and survival was 80%.

2. Naked Alfalfa Somatic Embryos Desiccated with Medium

The experimental protocol A.1 was duplicated with the addition that the somatic embryos were air dried on a filter paper raft suspended in half-strength Shenk and Hildebrandt liquid medium supplemented with 1.5% w/v maltose rather than 1.5% w/v sucrose. A piece of filter paper was folded and inserted into a Magenta Box (Magenta Corporation, Chicago, IL) such that the edges of the filter paper were in the liquid medium and the flat, central region of the paper was above the medium. At the beginning of air drying, the raft with embryos was suspended in 80 milliliter medium. After 20 days, the medium had evaporated to 68 milliliters. The somatic embryos produced plants at a 30% frequency as opposed to 21% for somatic embryos that were not air dried (control).

2a. As an alternative medium volume, 60 milliliters of medium were used. After 20 days, the medium had evaporated to 48 milliliters. The somatic embryos produced plants at a 41% frequency as opposed to 21% for the control.

2b. As an alternative medium volume, 40 milliliters of medium were used. After 20 days, the medium had evaporated to 25 milliliters. The somatic embryos produced plants at a 32% frequency as opposed to 21% for the control.

2c. As an alternative medium volume, 20 milliliters of medium were used. After 20 days, the medium had evaporated to 7 milliliters. The somatic embryos produced plants at a 33% frequency as opposed to 21% for the control.

3. Encapsulation of Desiccated Alfalfa Somatic Embryos

The experimental protocol of Example A,1, was duplicated, with the addition of a final step after somatic embryo desiccation in which the dried somatic embryos were suspended in a 2% (w/v) sodium alginate mixture and complexed in a 100 millimolar solution of calcium chloride to form calcium alginate beads. Somatic embryo germination was 57% of the total.

3a. As an alternative encapsulation medium, Tullanox TM (Tulco ®, Inc.), a fumed silica, was used to coat the desiccated somatic embryos by rolling the somatic embryos in Tullanox TM powder Somatic embryo survival was 42%.

4. Desiccation of Encapsulated Alfalfa Somatic Embryos

The experimental protocol of Example A,1, was duplicated, with the exception that the somatic embryos were encapsulated prior to desiccation, in a 2% alginate solution complexed in 100 millimolar calcium chloride. Somatic embryo survival was 90% of the total.

4a. As an alternative encapsulation matrix, 2% (w/v) sodium alginate was used to coat the somatic embryos prior to desiccation. Survival was 80%.

4b. As an alternative encapsulation matrix, 2% (w/v) Terra-Sorb ® (Industrial Services International, Inc.), was used to coat the somatic embryos prior to desiccation. Survival was 80%.

5. Protectants

The experimental protocol of Example A,4a., was duplicated, with the exception that 5% (w/v) dimethylsulfoxide was added to the sodium alginate mixture. Somatic embryo survival was 90%.

5a. As an alternative protectant, 10% (w/v) dextran was used. Somatic embryo survival was 50%.

6. Long-term Desiccation

The experimental protocol of Example A,1, was duplicated with the exception that the somatic embryos were desiccated slowly at 4° C. in a sealed petri dish with Shenk and Hildebrandt medium with 3% (w/v) sucrose, 10 millimolar ammonium, and 30 millimolar L-proline for 110 days. After 110 days, the medium had completely dried out. Somatic embryo survival was 27%.

7. Somatic Embryo Maturation

The experimental protocol of Example A,1, was duplicated with the exception that the somatic embryos after regeneration were placed on Schenk and Hildebrandt medium containing 3% (w/v) sucrose and 10 micromolar abscisic acid for a 14 day maturation period. Subsequently, the embryos were dried for 60 minutes in an open petri dish without medium. Afterwards, the embryos were placed on half-strength Schenk and Hildebrandt medium containing 1.5% (w/v) sucrose for germination. The embryos germinated at a frequency of 85% whereas embryos without the abscisic acid maturation treatment had a 0% germination frequency.

EXAMPLE B: (CELERY SOMATIC EMBRYOS)

1. Naked Somatic Embryos

Celery, *Apium graveolens* L. strain Calmario, callus was induced from hypocotyls and cotyledons of two-week old plants placed on Shenk and Hildebrandt medium containing 0.5 to 25 micromolar kinetin. Somatic embryos formed one to three months after transfer to Shenk and Hildebrandt medium containing 25 millimolar ammonium nitrate. The somatic embryos were matured on Shenk and Hildebrandt medium containing 12% sucrose in order to hold and maintain the embryos. The sucrose osmotic agent inhibited embryo germination. The embryos germinated after the osmotic agent was removed at a germination frequency equal to noninhibited embryos.

1a. As an alternative desiccation agent, 12% maltose was substituted for the sucrose. The maltose inhibited germination. After the osmotic agent was removed, the inhibited embryos germinated at a frequency equal to non-inhibited embryos.

1b. As an alternative desiccation agent, $10^{-4}$ to $10^{-7}$ millimolar abscisic acid was substituted for the sucrose. The abscisic acid inhibited germination. After the osmotic agent was removed, the inhibited embryos germinated at a frequency equal to noninhibited controls.

1c. As an alternative desiccation agent, 0.26 to 0.44 millimolar sodium chloride was substituted for the sucrose. The sodium chloride inhibited germination. After the osmotic agent was removed, the inhibited embryos terminated at a frequency equal to noninhibited controls.

1d. As an alternative desiccation agent, 0.04 to 0.4 molar mannitol was substituted for sucrose. The mannitol inhibited germination. After the osmotic agent was removed, the inhibited embryos germinated at a frequency equal to non-inhibited controls.

EXAMPLE C: (WILD MUSTARD ZYGOTIC EMBRYOS)

1. Naked Zygotic Embryos

Flower pods, two or four weeks after pollination, were removed from *Brassica campestris* L. plants growing in the wild. Zygotic embryos were dissected from the ovules contained within the flower pods and were placed on 20 milliliters agar-solidified Monnier's 12% (w/v) sucrose medium (M. Monnier, "Culture of Zygotic Embryos," Frontiers of Plant Tissue Culture, T. A. Thorpe, Ed., International Association for Plant Tissue Culture, University of Calgary, Alberta, Canada, pp. 277–280, 1980), which were then placed inside a sealed container holding 150 ml of Drierite for two weeks. The embryos did not germinate under these drying conditions but continued to mature. Upon transfer to Monnier's 2% sucrose medium, the embryos germinated at 100% frequency as compared with embryos that were not dried which germinated at 90%.

1a. As an alternative desiccant, 100 milliliters of a 3.43 molar solution of sulfuric acid was placed in the sealed container holding the isolated zygotic embryos. After drying, the embryos were transferred to Monnier's sucrose medium and germinated at a frequency equal to that of the non-desiccated embryos

2. Encapsulated Zygotic Embryos

The experimental protocol of Example C,1, was duplicated with the addition of the zygotic embryos being encapsulated in a 2% (w/v) sodium alginate solution complexed with the 100 millimolar calcium alginate. The encapsulated zygotic embryos were stored for two weeks in sealed container by including 12% (w/v) sucrose in the sodium alginate mixture. The encapsulated zygotic embryos readily germinated at a 75% frequency as compared with the control (60% germination) when placed on Shenk and Hildebrandt medium with 2% (w/v) sucrose.

2a. As an alternative germination inhibitor, $10^{-6}$ molar abscisic acid was substituted for sucrose. Germination was completely inhibited for 2 weeks. When the embryos were transferred to Monnier's 2% medium, the embryos germinated at 20% frequency.

3. Desiccation in Capsules

*Brassica camoestris* L. zygotic embryos were encapsulated as in the protocol Example C,2. The capsules were allowed to dry down over a solution of sulfuric acid for one week. At that time alginate had dried around the embryo and had a breaking strength of greater than 60 kg/cm² (compared to a breaking strength of 7-15 kg/cm² for newly encapsulated embryos). The dried capsules were placed on a medium with 2% w/v sucrose (see protocol of Example C,1), the embryos germinated, and plants were recovered at a 45% frequency as compared to 60% germination for the control.

Although the foregoing invention has been described in some detail for purposes of clarity of understanding, it will be appreciated that numerous modifications may be practiced while remaining within the spirit and scope of the appended claims.

We claim:

1. A process for creating an analog to natural botanic seed, which comprises:
   isolating totipotent meristematic tissue, which tissue has the potential to differentiate to produce an entire plant body;
   encapsulating said isolated meristematic tissue in a hydrated gel capsule which will permit development of said plant body; and
   dehydrating said gel capsule until the saturation level of the meristematic tissue is less than 99.9%.

2. The process according to claim 1 wherein said meristematic tissue is encapsulated substantially free from botanic accessory structures.

3. The process according to claim 2 wherein the meristematic tissue is derived from somatic tissue.

4. The process according to claim 3 wherein the somatic tissue is from a plant selected from the group consisting of *Medicago sativa* L., *Apium graveolens* L., and *Brassica camoestris* L.

5. The process according to claim 1 wherein said meristematic tissue is derived from zygotic tissue.

6. The process according to claim 1 wherein said meristematic tissue is derived from germ line tissue.

7. The process according to claim 1 wherein said meristematic tissue is tissue which has been induced to form shoot meristems.

8. The process according to claim 1 wherein said gel comprises one or more distinct gel agents.

9. The process according to claim 1 wherein said gel further comprises biologically active adjuvants in bioaffecting concentrations thereof.

10. The process according to claim 1 wherein the gel is selected from the group consisting of sodium alginate, sodium alginate complexed with a calcium salt, and Terra-Sorb ®.

11. The process according to claim 10 wherein a protectant is added to the gel, such protectant being selected from a group consisting of dimethylsulfoxide and dextran.

12. A process for creating an analog to natural botanic seed, which comprises:

isolating totipotent meristematic tissue, which tissue has the potential to differentiate to produce an entire plant body;

dehydrating said meristematic tissue such that the saturation level of the tissue is less than 99.9%; and, encapsulating said isolated, dehydrated meristematic tissue in a hydrated gel capsule which will permit development of said plant body.

13. The process of claim 12 further comprising dehydrating said hydrated gel capsule containing dehydrated meristematic tissue such that the saturation level of said gel is less than 99.9%.

14. The process according to claim 12 wherein said meristematic tissue is encapsulated substantially free from botanic accessory structures.

15. The process according to claim 12 wherein the meristematic tissue is derived from somatic tissue.

16. The process according to claim 12 wherein the somatic tissue is from a plant selected from the group consisting of *Medicago sativa* L., *Apium graveolens* L., and *Brassica campestris* L.

17. The process according to claim 12 wherein said meristematic tissue is derived from zygotic tissue.

18. The process according to claim 12 wherein said meristematic tissue is derived from germ line tissue.

19. The process according to claim 12 wherein said meristematic tissue is tissue which has been induced to form shoot meristems.

20. The process according to claim 12 wherein said gel comprises one or more distinct gel agents.

21. The process according to claim 12 wherein said gel further comprises biologically active adjuvants in bio-affecting concentrations thereof.

22. The process according to claim 12 wherein the gel is sodium alginate, complexed with a calcium salt.

23. The process according to claim 12 wherein the gel is fumed silica.

24. An analog to natural botanic seed which comprises:

meristematic tissue having the potential to differentiate into an entire plant body which is encapsulated in a hydrated gel capsule which will permit development of said body and which capsule is subsequently dehydrated such that the saturation level of such meristematic tissue is less than 99.9%.

25. An analog to natural botanic seed which comprises:

meristematic tissue having the potential to differentiate into an entire plant body which tissue is dehydrated such that the saturation level is less than 99.9% and which tissue is subsequently encapsulated in a hydrated gel capsule which will permit development of said body.

26. The analog according to claim 24 wherein said meristematic tissue is tissue selected from the group consisting of somatic tissue, zygotic tissue and germline tissue.

27. The analog according to claim 24 wherein said gel comprises one or more distinct gel agents.

28. The analog according to claim 24 wherein said gel further comprises biologically active adjuvants in bio-affecting concentrations thereof.

29. The analog according to claim 24 wherein said gel is selected from the group consisting of sodium alginate, sodium alginate complexed with a calcium salt, and Terra-Sorb ®.

30. The analog according to claim 25 wherein said meristematic tissue is tissue selected from the group consisting of somatic tissue, zygotic tissue and germline tissue.

31. The analog according to claim 25 wherein said gel comprises one or more distinct gel agents.

32. The analog according to claim 25 wherein said gel further comprises biologically active adjuvants in bio-affecting concentrations thereof.

33. The analog according to claim 25 wherein said gel is selected from the group consisting of sodium alginate complexed with a calcium salt and fumed silica.

* * * * *